United States Patent
Morgan et al.

(10) Patent No.: US 9,522,103 B2
(45) Date of Patent: Dec. 20, 2016

(54) ORAL CARE COMPOSITIONS

(75) Inventors: Andre Morgan, Robbinsville, NJ (US); Marilou Joziak, South River, NJ (US); Michael Prencipe, Princeton Junction, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/365,690

(22) PCT Filed: Dec. 20, 2011

(86) PCT No.: PCT/US2011/066074
§ 371 (c)(1),
(2), (4) Date: Jun. 16, 2014

(87) PCT Pub. No.: WO2013/095366
PCT Pub. Date: Jun. 27, 2013

(65) Prior Publication Data
US 2014/0356300 A1    Dec. 4, 2014

(51) Int. Cl.
| | | |
|---|---|---|
| *A61Q 11/00* | (2006.01) | |
| *A61K 8/21* | (2006.01) | |
| *A61K 8/86* | (2006.01) | |
| *A61K 8/24* | (2006.01) | |
| *A61K 8/25* | (2006.01) | |
| *A61K 8/362* | (2006.01) | |
| *A61K 8/368* | (2006.01) | |
| *A61K 8/46* | (2006.01) | |
| *A61K 8/49* | (2006.01) | |
| *A61K 8/81* | (2006.01) | |

(52) U.S. Cl.
CPC . *A61K 8/21* (2013.01); *A61K 8/24* (2013.01); *A61K 8/25* (2013.01); *A61K 8/362* (2013.01); *A61K 8/368* (2013.01); *A61K 8/463* (2013.01); *A61K 8/49* (2013.01); *A61K 8/81* (2013.01); *A61K 8/86* (2013.01); *A61Q 11/00* (2013.01)

(58) Field of Classification Search
CPC .................................. A61Q 11/00; A61K 8/21
See application file for complete search history.

(56) References Cited

U.S. PATENT DOCUMENTS

| | | | |
|---|---|---|---|
| 3,538,230 A | 11/1970 | Pader et al. | |
| 3,862,307 A | 1/1975 | Di Giulio | |
| 4,340,583 A | 7/1982 | Wason | |
| 4,568,540 A | 2/1986 | Asano et al. | |
| 5,112,599 A * | 5/1992 | Coulson | 424/52 |
| 5,188,820 A | 2/1993 | Cummins et al. | |
| 5,188,821 A | 2/1993 | Gaffar et al. | |
| 5,192,531 A | 3/1993 | Gaffar et al. | |
| 5,476,647 A | 12/1995 | Chow et al. | |
| 5,624,906 A * | 4/1997 | Vermeer | 514/23 |
| 5,653,964 A | 8/1997 | Herms et al. | |
| 5,788,951 A | 8/1998 | Blake-Haskins et al. | |
| 5,849,269 A * | 12/1998 | Burgess et al. | 424/52 |
| 5,900,230 A | 5/1999 | Cutler | |
| 6,159,449 A | 12/2000 | Winston et al. | |
| 6,346,235 B1 | 2/2002 | Joziak et al. | |
| 2004/0126335 A1* | 7/2004 | Faller et al. | 424/52 |
| 2006/0134025 A1* | 6/2006 | Trivedi et al. | 424/58 |
| 2007/0218018 A1 | 9/2007 | MacDonald | |
| 2008/0187500 A1 | 8/2008 | Karlinsey | |
| 2008/0260836 A1 | 10/2008 | Boyd | |
| 2010/0291164 A1 | 11/2010 | Karlinsey | |

FOREIGN PATENT DOCUMENTS

| | | |
|---|---|---|
| EP | 0190762 | 8/1986 |
| WO | WO 99/63961 | 12/1999 |
| WO | WO0032160 | 6/2000 |
| WO | WO 01/34107 | 5/2001 |
| WO | WO 01/34108 | 5/2001 |
| WO | WO 01/68046 | 9/2001 |
| WO | WO 2004/054531 | 7/2004 |
| WO | WO2004054530 | 7/2004 |
| WO | WO2005037241 | 4/2005 |
| WO | WO2008013719 | 1/2008 |
| WO | WO2009117644 | 9/2009 |

OTHER PUBLICATIONS

International Search Report and the Written Opinion issued in International Application PCT/US2011/066074 mailed Oct. 10, 2012.
Written Opinion of the International Preliminary Examining Authority issued in International Application PCT/US2011/066074 mailed Jan. 27, 2014. WO.
Oral-B Laboratories, 2000, "Minute Foam," Package Label Principal Display Panel, www.dentalcare.com.
Schemehorn et al., 1990, "A Bovine Enamel Model for in vitro Remin/Demin Tests," Journal of Dental Research, vol. 69, p. 260, Abstract No. 1213.
Schemehorn et al., 1992, "Fluoride Update and Remineralization in Human and Bovide Enamel," Journal of Dental Research (IADR Abstracts), vol. 71, p. 186 Abstract No. 644.
Schemehorn et al., 1994, "An in-vitro Remin/Demin Model Showing a Fluoride Dose Response," Journal of Dental Research (IADR Abstracts), vol. 73, p. 241, Abstract No. 1117.

* cited by examiner

*Primary Examiner* — Frederick Krass
*Assistant Examiner* — Tracy Liu

(57) ABSTRACT

Disclosed herein are compositions comprising a fluoride ion source, a poly(propylene oxide)/poly(ethylene oxide) copolymer, and optionally a sparingly soluble acid; and methods of using and of making the same.

17 Claims, No Drawings

ORAL CARE COMPOSITIONS

CROSS-REFERENCE TO RELATED PATENT APPLICATIONS

The present application is a U.S. national stage entry under 35 USC. §371 of Patent Cooperation Treaty Patent Application No. PCT/US2011/66074, filed Dec. 20, 2011, the entirety of which is incorporated herein by reference.

BACKGROUND

Fluoride is one of the best known agents used to combat dental caries. In order for fluoride to be effective it must be soluble in the formula and efficiently delivered to the enamel surface upon dilution. The choice of formulation ingredients plays a key role in determining whether or not fluoride is effectively delivered to the enamel surface upon use. It is therefore critical to choose the appropriate type and level of formula excipients to ensure that one gets the full benefit of the fluoride incorporated in a product.

SUMMARY

The present inventors have discovered that incorporating nonionic block copolymers (i.e., poloxomers) alone or in combination with sparingly soluble acids into a fluoride containing formulation enhances the bioavailability of fluoride therefrom and subsequently enhances fluoride uptake and remineralization of enamel surfaces using these formulations.

Some embodiments of the present invention provide an oral care composition comprising: a fluoride ion source, an effective amount of a polypropylene oxide)/poly(ethylene oxide) copolymer; and optionally, an effective amount of a sparingly soluble acid for enhancing fluoride delivery.

Other embodiments provide methods of enhancing delivery of fluoride to tooth enamel comprising applying an effective amount of any of the compositions described herein to the oral cavity of a subject in need thereof.

Still further embodiments provide methods of enhancing protection of teeth against caries and cavities and increasing resistance to acid demineralization comprising administering to the oral cavity, of a subject in need thereof, a composition as described herein.

Yet other embodiments provide the use of a composition as described herein for the manufacture of a medicament for enhancing protection of teeth against caries and cavities and increasing resistance to acid demineralization.

In some embodiments, the compositions demonstrate a Vickers Hardness Number ("VHN"), which correlates with an acceptable level of enamel remineralization.

DETAILED DESCRIPTION

The pH of a dentifrice, such as a toothpaste or gel, should be at or near neutral in order for the formulation to maintain stability prior to use. However, fluoride delivery to the tooth enamel is enhanced at a more acidic pH. It has been surprisingly discovered that the addition of an appropriate amount of block copolymer to a fluoride containing composition will provide a stable composition on storage (maintaining a near neutral pH), but will lower the pH of the composition upon use to an extent sufficient to enhance delivery of fluoride ions to the tooth enamel. Such enhanced delivery of fluoride ions to teeth results in remineralization of tooth enamel surfaces.

As used herein, the term "enhanced delivery" or "enhancing the delivery" refers to the increased availability or uptake of an ingredient at the target site, e.g. increased uptake of fluoride in tooth enamel.

The present inventors have surprisingly discovered that the presence of certain amounts of a block copolymer and a sparingly soluble acid in a fluoride containing composition, provides a composition which: (1) is stable during packaging and storage; (2) demonstrates a reduced pH upon dilution in an aqueous liquid (e.g. during brushing); thereby providing enhanced delivery of fluoride to the tooth enamel.

In some embodiments, compositions of the present invention have a pH, prior to use, of from about 5 to about 9. In some embodiments, compositions of the present invention have a pH, prior to use, of from about 6 to about 8. In other embodiments, compositions of the present invention have a pH, prior to use, of from about 6.7 to about 7.3. In further embodiments, compositions of the present invention have a pH, prior to use, of from about 6.8 to about 7.2. In some embodiments, compositions of the present invention have a pH, prior to use, of about 7.

In some embodiments, the present invention provides compositions which are single-phase compositions.

During typical use a composition of the invention such as a dentifrice is diluted in an aqueous liquid, e.g., water or saliva, to about 3:1, wherein the ratios are liquid:composition. In some embodiments, the pH of the compositions decrease by from about 0.6 to about 1.5 pH units, during use. In some embodiments, the pH of the compositions decrease by from about 0.7 to about 1.4 pH units. In some embodiments, the pH of the compositions decrease by from about 0.8 to about 1.3 pH units, during use. In some embodiments, the pH of the compositions decrease by from about 0.9 to about 1.2 pH units, during use. In some embodiments, the pH of the compositions decrease by about 1 pH unit, during use.

In some embodiments, the time period of use is from about 15 seconds to about 180 seconds. In some embodiments, the time period of use is from about 30 seconds to about 120 seconds. In some embodiments, the time period of use is about 45 seconds. In some embodiments, the time period of use is about 60 seconds. In some embodiments, the time period of use is about 90 seconds. In some embodiments, the time period of use is about 120 seconds.

In some embodiments, enamel fluoride uptake (EFU) is evaluated using FDA Monograph #40. In some embodiments, EFU can be evaluated using any suitable means known to those skilled in the art.

In some embodiments, the compositions of the present invention comprise a fluoride ion source and a polypropylene oxide)/poly(ethylene oxide) copolymer, wherein the copolymer is present in an amount effective to provide a stable formulation on storage and deliver an effective amount of fluoride during use. In some embodiments, the copolymer is present in an amount effective to maintain the pH of the composition in the range of from about 6.5 to about 7.5. In some embodiments, the copolymer is present in an amount effective to reduce the pH by about 1 pH unit during use.

In some embodiments, the copolymer is present in an amount effective to provide an enamel fluoride uptake (e.g. EFU) of at least about 40% of the theoretical fluoride concentration contained in the initial formulation. In some embodiments, the copolymer is present in an amount effective to provide an EFU of at least 30% greater than a suitable control.

In some embodiments, the copolymer is selected from: Poloxamer 338, Poloxamer 407, Poloxamer, 237, Poloxamer, 217, Poloxamer 124, Poloxamer 184, Poloxamer 185, and a combination of two or more thereof. In some embodiments, the copolymer is Poloxamer 338. In some embodiments, the copolymer is Poloxamer 407. In some embodiments, the copolymer is Poloxamer 188. In some embodiments, the copolymer is Poloxamer 124.

In some embodiments, the copolymer is present in the amount of about 0.1 to about 10% of the total composition weight. In some embodiments, the copolymer is present in the amount of about 2.5% to about 5% of the total composition weight. In some embodiments, the copolymer is present in the amount of about 2.5% of the total composition weight. In some embodiments, the copolymer is present in the amount of 5% of the total composition weight.

Some embodiments of the present invention further comprise an effective amount of a sparingly soluble acid. As used herein, the term "sparingly soluble acid" means an acid having a water solubility of about 0.1 g/100 ml to about 30 g/100 ml in water at 25° C. In some embodiments, the sparingly soluble acid has a water solubility of about 0.5 g/100 ml to about 15 g/100 ml in water at 25° C.

In some embodiments, the sparingly soluble acid is an organic sparingly soluble acid. In other embodiments, the sparingly soluble acid is an acid phosphate salt. In some embodiments, the sparingly soluble acid is sodium acid pyrophosphate, sodium aluminum phosphate, monopotassium phosphate, or a mixture thereof. In some embodiments, the sparingly soluble acid is selected from: fumaric acid, propionic acid, pentanoic acid, and a combination of two or more thereof. In some embodiments, the sparingly soluble acid is fumaric acid.

In some embodiments, the sparingly soluble acid is present in an amount of about 0.01 to less than about 0.5%, of the total composition weight. In some embodiments, the sparingly soluble acid is present in an amount of about 0.0125 to less than about 0.5% of the total composition weight. In some embodiments, the sparingly soluble acid is present in an amount of about 0.05 to less than about 0.5% of the total composition weight. In some embodiments, the sparingly soluble acid is present in an amount of about 0.1 to less than about 0.5% of the total composition weight. In some embodiments, the sparingly soluble acid is present in an amount of about 0.25 to less than about 0.5% of the total composition weight. In some embodiments, the sparingly soluble acid is present in an amount of about 0.05% of the total composition weight.

In some embodiments, the fluoride ion source is selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and a combination of two or more thereof.

In some embodiments, the fluoride ion source is selected from sodium fluoride and sodium monofluorophosphate. In some embodiments, the fluoride ion source comprises sodium fluoride. In some embodiments, the fluoride ion source is present in an amount of about 0.01% to about 2% of the total composition weight. In some embodiments, the fluoride ion source is present in an amount of about 0.1% to about 0.2% of the total composition weight.

In some embodiments, the fluoride ion source is present in an amount effective to provide greater than about 1000 ppm fluoride ion. In some embodiments, the fluoride ion source is present in an amount effective to provide greater than about 2000 ppm fluoride ion. In some embodiments, the fluoride ion source is present in an amount effective to provide greater than 2250 ppm fluoride ion. In some embodiments, the fluoride ion source is present in an amount effective to provide greater than about 2500 ppm fluoride ion. In some embodiments, the fluoride ion source is present in an amount effective to provide greater than about 2750 ppm fluoride ion.

In some embodiments, the compositions further comprise a calcium ion source. In some embodiments, the calcium ion source is selected from: tricalcium phosphate, hydroxyapatite, dicalcium phosphate dehydrate, calcium pyrophosphate, amorphous calcium phosphate, and a combination of two or more thereof. In some embodiments, the calcium ion source comprises tricalcium phosphate.

In some embodiments, the compositions comprise from about 0.01% to about 10% by weight of a calcium ion source. In other embodiments, the composition comprises from about 0.01% to about 1% by weight of a calcium ion source. In further embodiments, the composition comprises from about 0.02% to about 0.2% by weight of a calcium ion source. In some embodiments, the composition comprises about 0.0775%, by weight, of a calcium ion source.

Some embodiments of the present invention comprise an abrasive. In some embodiments, the abrasive is selected from: sodium bicarbonate, calcium phosphate (e.g., dicalcium phosphate dihydrate), calcium sulfate, precipitated calcium carbonate, silica (e.g., hydrated silica), iron oxide, aluminum oxide, coated alumina, perlite, and a combination of two or more thereof. In some embodiments, the compositions comprise from about 15% to about 70% of the total composition weight.

In some embodiments, the compositions comprise an abrasive having a small particle (d50 of <5 micrometers) fraction of at least about 5%.

Some embodiments provide a composition comprising an anionic surfactant selected from: a. water-soluble salts of higher fatty acid monoglyceride monosulfates (e.g., the sodium salt of the monosulfated monoglyceride of hydrogenated coconut oil fatty acids such as sodium N-methyl N-cocoyl taurate, sodium cocomono-glyceride sulfate); b. higher alkyl sulfates, e.g., sodium lauryl sulfate; c. higher alkyl-ether sulfates, e.g., of formula $CH_3(CH_2)_mCH_2(OCH_2CH_2)_nOSO_3X$, wherein m is 6-16, e.g., 10, n is 1-6, e.g., 2, 3 or 4, and X is Na or K (for example sodium laureth-2 sulfate $(CH_3(CH_2)_{10}CH_2(OCH_2CH_2)_2OSO_3Na)$); d. higher alkyl aryl sulfonates (such as sodium dodecyl benzene sulfonate (sodium lauryl benzene sulfonate)); e. higher alkyl sulfoacetates (such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate); f. and mixtures thereof.

By "higher alkyl" is meant, e.g., $C_{6-30}$ alkyl. In some embodiments, the anionic surfactant is selected from sodium lauryl sulfate and sodium ether lauryl sulfate.

In some embodiments, the anionic surfactant is present in an amount of from about 0.3% to about 4.5% by weight of the composition.

Some embodiments further comprise a surfactant selected from a cationic surfactant, a zwitterionic surfactant, a nonionic surfactant, and a combination of two or more thereof.

In some embodiments, the compositions further comprise a humectant. In some embodiments, the humectant is selected from glycerin, sorbitol, xylitol and a combination of two or more thereof. In some embodiments, the composition comprises xylitol.

In some embodiments, the compositions further comprise a polymer in addition to the poly(propylene oxide)/poly(ethylene oxide) block copolymer. In some embodiments, the additional polymer is selected from a polyethylene glycol, a polyvinylmethyl ether maleic acid copolymer, a polysaccharides (e.g., a cellulose derivative, for example carboxymethyl cellulose, or a polysaccharide gum, e.g., xanthan gum or carrageenan gum), and a combination of two or more thereof.

Some embodiments further comprise an antibacterial agent selected from a halogenated diphenyl ether (e.g. triclosan), a magnolol derivative, an herbal extract or essential oil (e.g., rosemary extract, tea extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), a bisguanide antiseptic (e.g., chlorhexidine, alexidine or octenidine), a quaternary ammonium compound (e.g., cetylpyridinium chloride (CPC), benzalkonium chloride, tetradecylpyridinium chloride (TPC), N-tetradecyl-4-ethyl-pyridinium chloride (TDEPC)), a phenolic antiseptic, hexetidine, octenidine, sanguinarine, povidone iodine, delmopinol, salifluor, metal ions (e.g., zinc salts, for example, zinc citrate, a stannous salt, a copper salt, an iron salt), sanguinarine, propolis and an oxygenating agent (e.g., hydrogen peroxide, buffered sodium peroxyborate or peroxycarbonate), phthalic acid or a salt thereof, monoperthalic acid or a salt or ester thereof, ascorbyl stearate, oleoyl sarcosine, alkyl sulfate, dioctyl sulfosuccinate, salicylanilide, domiphen bromide, delmopinol, octapinol or another piperidino derivative, a nicin preparation, a chlorite salt; and a combination of two or more thereof.

In some embodiments, the antibacterial agent is present in an amount of about 0.01% to about 5% of the total composition weight. In other embodiments, the antibacterial is triclosan. In some embodiments, the triclosan is present in an amount of 0.01 to 1% of the total composition weight. Some embodiments provide compositions wherein the triclosan is present in the amount of about 0.3% of the total composition weight.

Some embodiments of the present invention provide methods to: (i) reduce or inhibit formation of dental caries, (ii) reduce, repair or inhibit pre-carious lesions of the enamel, e.g., as detected by quantitative light-induced fluorescence (QLF) or electrical caries measurement (ECM) (iii) reduce or inhibit demineralization and promote remineralization of the teeth, (iv) reduce or inhibit gingivitis, (v) clean the teeth and oral cavity (vi) reduce erosion, (vii) whiten teeth; and/or (viii) promote whole body health.

In some embodiments, the composition is in the form of a toothpaste.

Some embodiments further comprise an anti-calculus agent. In some embodiments, the anti-calculus agent is a polyphosphate, e.g., pyrophosphate, tripolyphosphate, or hexametaphosphate, e.g., in sodium salt form.

In some embodiments, the compositions include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof.

The silica abrasives useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference.

In some embodiments, the abrasive materials comprise a large fraction of very small particles, e.g., having a d50<5 microns, for example, small particle silica (SPS) having a d50 of about 3 to about 4 microns, for example Sorbosil AC43® (Ineos). Such small particles are particularly useful in formulations targeted at reducing hypersensitivity. The small particle component may be present in combination with a second larger particle abrasive. In certain embodiments, for example, the formulation comprises about 3 to about 8% SPS and about 25 to about 45% of a conventional abrasive.

Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention. The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide.

The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent can be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

In some embodiments, when noncationic antibacterial agents or antibacterial agents, e.g., triclosan, are included in any of the dentifrice components, there may also be included from about 0.05 to about 5% of an agent which enhances the delivery and retention of the agents to, and retention thereof on oral surfaces. Such agents useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 30,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight.

Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

In some embodiments, the compositions of the present invention can be manufactured as follows. Poloxamer is first dissolved in formula amount of water. Next, fluoride salts, sweeteners, and any other water soluble excipients are added to the poloxamer containing mixture, and mixed until dissolved. In a separate vessel, polymer gums/binding agents are added to the humectants, and mixed until dispersed. The polymer/humectant mixture is then added to the poloxamer/salt mixture described above, and mixed to create the gel phase. The abrasives are then added to the gel phase in a suitable vessel and mixed under vacuum to create a smooth dentifrice. Finally, surfactants, flavoring agent, and sparingly soluble acid are added to the dentifrice, and mixed under vacuum until homogeneous.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

Table 1 (below) describes the formulations of a composition according to some embodiments of the present invention (Formulae I-VI) and comparative examples (CI-CIV).

TABLE 1

| Ingredient | I | II | III | IV | V | VI | CI | CII | CIII | CIV |
|---|---|---|---|---|---|---|---|---|---|---|
| Sorbitol | 39.5 | 39.5 | 39.5 | 39.5 | 39.5 | 39.5 | 39.5 | 39.5 | 39.5 | 39.5 |
| Water | QS | QS | QS | QS | QS | QS | QS | QS | QS | QS |
| Abrasive silica | 8 | 8 | 8 | 8 | 8 | 8 | 8 | 8 | 8 | 8 |
| Silica thickener | 3 | 3 | 3 | 3 | 3 | 3 | 3 | 3 | 3 | 3 |
| Polyethylene glycol 600 | 3 | 3 | 3 | 3 | 3 | 3 | 3 | 3 | 3 | 3 |
| Sodium lauryl sulfate | 1.2 | 1.2 | 1.2 | 1.2 | 1.2 | 1.2 | 1.2 | 1.2 | 1.2 | 1.2 |
| Sodium fluoride | 1.105 | 1.105 | 1.105 | 1.105 | 1.105 | 1.105 | 1.105 | 1.105 | 1.105 | 1.105 |
| Flavor | 1 | 1 | 1 | 1 | 1 | 1 | 1 | 1 | 1 | 1 |
| Xanthan gum | 0.8 | 0.8 | 0.8 | 0.8 | 0.8 | 0.8 | 0.8 | 0.8 | 0.8 | 0.8 |
| Sodium benzoate | 0.5 | 0.5 | 0.5 | 0.5 | 0.5 | 0.5 | 0.5 | 0.5 | 0.5 | 0.5 |
| Sodium saccharin | 0.35 | 0.35 | 0.35 | 0.35 | 0.35 | 0.35 | 0.35 | 0.35 | 0.35 | 0.35 |
| PEO-PPO Block Copolymer | 5 | 5 | 5 | 5 | 5 | 5 | — | 1.5 | 5 | 5 |
| Fumaric acid | — | 0.05 | 0.0125 | 0.35 | — | 0.05 | — | 0.05 | 0.5 | — |
| Sodium acid pyrophosphate | — | — | — | — | 0.25 | — | — | — | — | 0.5 |
| Tricalcium Phosphate | | | | | | 0.0775 | | | | |

TABLE 1-continued

| Ingredient | I | II | III | IV | V | VI | CI | CII | CIII | CIV |
|---|---|---|---|---|---|---|---|---|---|---|
| Sodium Phosphate Monobasic | | | | | | | 1.05 | | | |
| Tetrapotassium Pyrophosphate | | | | | | | 0.63 | | | |
| Sodium Hydroxide-50% FCC | | | | | | | 0.5 | | | |

Example 2

Enamel fluoride uptake (EFU) is evaluated according to FDA Monograph Method #40, except the carries lesion was formed using a solution that is 0.1M lactic acid and 0.2% Carbopol 907 and is 50% saturated with hydroxyapatite (HAP) at a pH of 5.0. The method involved first forming an artificial caries lesion on the enamel specimens using the lesion forming solution described above. The specimens were then rinsed with deionized water, and subsequently treated with a slurry (1 part paste: 3 parts water) of the respective dentifrice. Next, the treated specimens were etched with a $HClO_4$ solution for 15 seconds to remove the delivered fluoride ion; the etching solution was then buffered with Total Ionic Strength Adjustment Buffer (TISAB) to pH 5.2, and analyzed for fluoride ions by ion selective electrode (ISE). Fluoride content was determined for each solution based on a calibration curve.

TABLE 2

| Composition | Avg EFU | STDEV |
|---|---|---|
| CI | 1430 | 57 |
| I | 2293 | 59 |
| II | 2883 | 76 |

The data described in Table 2 (above) demonstrates that compositions of the present invention deliver fluoride to the enamel to a significantly greater extent than compositions which do not contain the inventive combinations described herein.

Example 3

In addition to enamel fluoride uptake, the compositions are also analyzed for their ability to promote enamel lesion remineralization using the Vickers Hardness methodology, which simulates in vivo caries formation. This experiment involves a cyclic treatment regimen, consisting of 4 hr/day acid challenge of the enamel specimens using a demineralization solution, and four one minute dentifrice treatment. After the treatments, the specimens are rinsed with DI water and stored in remineralizing solution. The regimen is repeated for 20 days. After 20 days, the degree of remineralization is determined by measuring the change in surface micro hardness of the specimens following treatment and the initial micro hardness.

Table 3 (below) illustrates the change in surface micro hardness after 20 days treatment. The data described in Table 3 demonstrates that an exemplary composition of the present invention (Formula II) promotes enamel lesion remineralization to a significantly greater extent after 20 days, than a fluoride containing composition which does not contain the inventive combinations described herein.

TABLE 3

| Composition | Hardness (VHN) | STD |
|---|---|---|
| CI | 10.7 | 1.1 |
| II | 61.1 | 3.9 |

Example 4

Exemplary compositions of the present invention, which contain a calcium ion source, are also analyzed for their ability to promote enamel lesion remineralization using the Vickers Hardness methodology. The experiment is conducted as described in Example 3 (above). The regimen is repeated for 10 days. After 10 days, the degree of remineralization is determined by measuring the change in surface micro hardness of the specimens following treatment and the initial micro hardness.

The data described in Table 4 (below) further illustrates that exemplary compositions of the present invention (e.g. Formulae II and VI) promote enamel lesion remineralization to a significantly greater extent after 10 days, than a fluoride containing composition which does not contain the inventive combinations described herein.

TABLE 4

| Composition | Hardness (VHN) | STD |
|---|---|---|
| CI | 12.9 | 1.0 |
| II | 53.1 | 4.0 |
| VI | 70.9 | 6.8 |

Example 5

Exemplary compositions of the present invention are evaluated for their ability to provide fluoride stability to the formulation. The results are reported in Table 5 (below).

TABLE 5

| Composition | Initial pH | Soluble Fluoride Initial | Soluble Fluoride 3 Mon 40° C. |
|---|---|---|---|
| CIV | 6.93 | 3720 | n/a |
| Formula II | 7.18 | 5206 | 5200 |
| Formula V | 7.13 | 4808 | 4703 |

The data described in Table 5 (above) demonstrates that compositions of the present invention (e.g. Formula II and Formula V), provide >90% soluble fluoride recovery upon accelerated aging, while a comparative composition (CIV) that does not include the inventive combinations discovered by the present inventors, is unable to maintain an adequate level of fluoride stability.

The invention claimed is:

1. An oral care composition comprising:
   a fluoride ion source;
   fumaric acid in an amount effective to enhance delivery of fluoride to the enamel; and
   a poly(propylene oxide)/poly(ethylene oxide) copolymer in an amount effective to provide greater than 90% recovery of soluble fluoride ions after 3 months at 40° C.,
   wherein the poly(propylene oxide)/poly(ethylene oxide) copolymer is present in an amount of from about 0.1% to about 10%, by weight, of the composition and
   wherein the fumaric acid is present in an amount of from about 0.01 to about 0.5%, by weight, of the composition.

2. The composition of claim 1, wherein the poly(propylene oxide)/poly(ethylene oxide) copolymer has a molecular weight of from about 8,000 to about 18,000 g/mol, and an ethylene oxide content of from about 30 to about 90%, by weight of the copolymer.

3. The composition of claim 1, wherein the poly(propylene oxide)/poly(ethylene oxide) copolymer has a molecular weight of from about 12,000 to about 15,000 g/mol, and an ethylene oxide content of from about 70 to about 80%, by weight of the copolymer.

4. The composition of claim 1, wherein the poly(propylene oxide)/poly(ethylene oxide) copolymer is selected from: Poloxamer 237; Poloxamer 217; Poloxamer 184; Poloxamer 185; Poloxamer 188; Poloxamer 338; Poloxamer 407; and a combination of two or more thereof.

5. The composition of claim 2, wherein the poly(propylene oxide)/poly(ethylene oxide) copolymer is selected from Poloxamer 237; Poloxamer 188; Poloxamer 338; Poloxamer 407; and a combination of two or more thereof.

6. The composition of claim 1, wherein the poly(propylene oxide)/poly(ethylene oxide) copolymer is selected from: Poloxamer 338; Poloxamer 407; and a combination of two or more thereof.

7. The composition of claim 1, wherein the fumaric acid is present in an amount of from about 0.01 to about 0.25%, of the total composition weight.

8. The composition of claim 1, wherein the fluoride ion source is selected from stannous fluoride, sodium fluoride, potassium fluoride, sodium monofluorophosphate, sodium fluorosilicate, ammonium fluorosilicate, amine fluoride, ammonium fluoride, titanium fluoride, hexafluorosulfate, silver diamine fluoride, indium 10 fluoride, zinc fluoride, and a combination of two or more thereof.

9. The composition of claim 1, wherein the fluoride ion source is present in an amount of about 0.01 wt. % to about 2 wt. % of the total composition weight.

10. The composition of claim 1, wherein the pH is about 6.5 to about 7.5 in undiluted form, and wherein the pH of the composition is lowered from about 0.6 to about 2 pH units, during use.

11. The composition of claim 1, further comprising a calcium ion source.

12. The composition of claim 11, wherein the calcium ion source is tricalcium phosphate hydroxyapatite, dicalcium phosphate dihydrate, calcium pyrophosphate, amorphous calcium phosphate, or mixtures thereof present in an amount of about 0.01 to about 1% of the total composition weight.

13. The composition of claim 1, in a form selected from: a mouthrinse, a toothpaste, a tooth gel, a tooth powder, a non-abrasive gel, an oral care mousse, a foam, mouth spray, a lozenge, a tablet, a dental implement, and a pet care product.

14. A method of enhancing delivery of fluoride to tooth enamel comprising applying an effective amount of the composition according to claim 1 to the oral cavity of a subject in need thereof.

15. A method of enhancing protection of teeth against caries and cavities and increasing resistance to acid demineralization comprising administering to the oral cavity, of a subject in need thereof, a composition according to claim 1.

16. A composition according to claim 1 for use in enhancing protection of teeth against caries and cavities and increasing resistance to acid demineralization.

17. A composition according to claim 1, wherein the poly(propylene oxide)/poly(ethylene oxide) copolymer is present in an amount of from about 2.5% to about 5%, by weight, of the composition.

* * * * *